Figure 1:
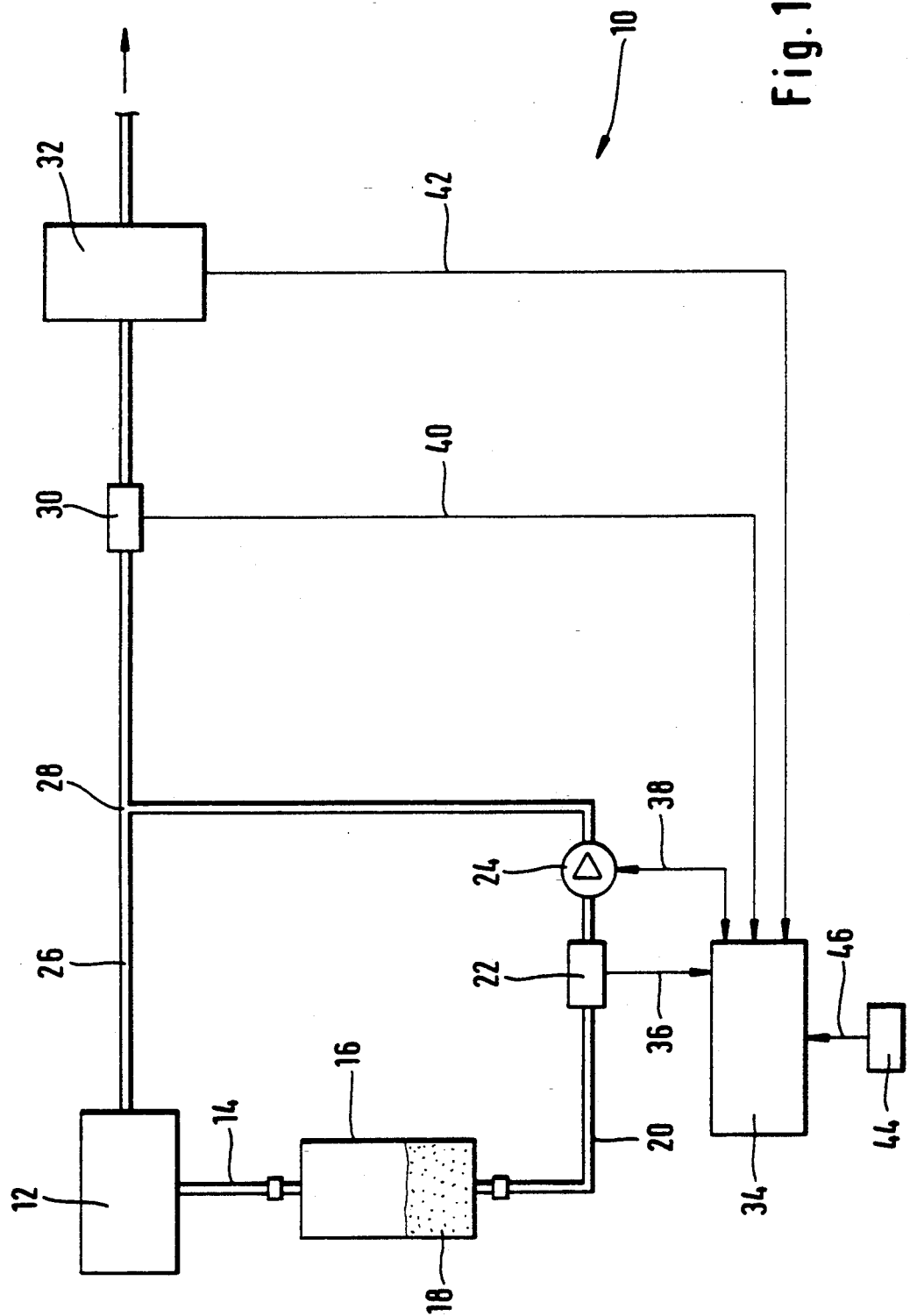

United States Patent [19]

Polaschegg et al.

[11] Patent Number: 5,295,505
[45] Date of Patent: Mar. 22, 1994

[54] APPARATUS FOR PREPARATION OF A MEDICINAL SOLUTION

[75] Inventors: Hans-Dietrich Polaschegg, Oberursel; Claus Walter, Bad Homburg, both of Fed. Rep. of Germany

[73] Assignee: Fresenius Ag, Bad Homburg, Fed. Rep. of Germany

[21] Appl. No.: 967,000

[22] Filed: Oct. 27, 1992

[30] Foreign Application Priority Data

Nov. 28, 1991 [DE] Fed. Rep. of Germany ....... 4139165

[51] Int. Cl.⁵ .............................................. A61M 1/14
[52] U.S. Cl. .................................. 137/93; 210/321.71
[58] Field of Search .................. 137/93, 5; 210/321.71

[56] References Cited

U.S. PATENT DOCUMENTS

| | | | |
|---|---|---|---|
| 3,352,779 | 11/1967 | Austin | 137/5 X |
| 3,847,809 | 11/1974 | Kopf | 210/321.71 X |
| 4,895,657 | 1/1990 | Polaschegg | 210/32.71 X |

FOREIGN PATENT DOCUMENTS

| | | |
|---|---|---|
| 0278100 | 8/1988 | European Pat. Off. . |
| 8607304.4 | 9/1986 | Fed. Rep. of Germany . |
| 3734880C1 | 3/1989 | Fed. Rep. of Germany . |
| 3911587A1 | 10/1990 | Fed. Rep. of Germany . |

OTHER PUBLICATIONS

DE-Z Biomedizinische Technik, vol. 29, Issue 6 (1984) p. 166.
DE-Z: Medizintechnik, 105, Jahrgang Nr. 4 (1985), pp. 113–118.

Primary Examiner—Robert G. Nilson
Attorney, Agent, or Firm—Robbins, Berliner & Carson

[57] ABSTRACT

An apparatus for preparing a medicinal solution, in particular dialysis solution, from pulverulent concentrate and water comprises a water source (12) from which a first conduit (14) is led to a container which contains the powder and from which a second conduit (20) into which a first measuring cell (22) and a concentrate pump (24) are connected leads to a mixing point (28). Said mixing point (28) is located in a third conduit (26) which leads from the water source to a consumer; downstream of the mixing point (28) a second measuring cell (30) is provided for monitoring the composition of the finished dialysis solution. Since the two measuring cells (22) and (30) lie in different conduits in which solutions of different composition are conveyed, there is no possibility whatever of confusions between concentrates of the same initial conductivity but different final conductivity after dilution with water.

8 Claims, 3 Drawing Sheets

APPARATUS FOR PREPARATION OF A MEDICINAL SOLUTION

The invention relates to an apparatus for preparation of a medicinal solution, in particular a dialysis solution, from a pulverulent concentrate and water. It comprises a water source, a first conduit from the water source to a container containing the pulverulent concentrate, a second conduit extending from the container to a mixing point which is disposed in a third conduit originating from the water source, a concentrate conveying means connected into the second conduit, a solution conveying means in the third conduit downstream of the mixing point, a mixing cell in the conduit system, a control unit controlling the concentrate conveying means in predetermined manner in response to the signal of the measuring cell, and a protective system which disconnects the apparatus in the event of an incorrect composition of the solution.

It is known to prepare medicinal solutions, in particular solutions for hemodialysis, from one or more liquid concentrates and water. This is the case in particular with bicarbonate-containing dialysis solutions because their constituents do not remain fully in solution in concentrated form.

In EP-A-0 278 100 an apparatus of the type mentioned at the beginning is described in which the dialysis solution is prepared in that water is conducted into a container containing a pulverulent concentrate in which it dissolves up to the saturation limit of the pulverulent constituents. The liquid salt concentrate is then further diluted with water down to a desired concentration. For this purpose, the liquid concentrate is mixed with water at a mixing point, whereupon the mixture obtained is supplied downstream of the mixing point to a conductivity cell. The signal of the conductivity cell is transmitted to a control unit which compares the signal obtained with a predetermined value and in the event of a deviation from a desired value controls a concentrate conveying means, usually constructed as concentrate pump, in such a manner that a defined predetermined conductivity arises downstream of the mixing point, i.e. the dialysis solution has a predetermined composition.

Furthermore, such an apparatus comprises a protective system against incorrect composition of the dialysis solution, said system being arranged in the outgoing conduit and monitoring the composition of the finished dialysis solution. For this purpose, as a rule conductivity measuring cells are also employed which to protect the patient from dialysis with unsuitable dialysis solution (guide-lines according to VDE 750, part 206 or part 213) must be independent of the conductivity cell used for controlling the composition of the dialysis solution.

Now, if the control of the composition of the dialysis solution is carried out with a sensor determining the final composition of the dialysis solution, as is illustrated in aforementioned EP 0 278 100, and if furthermore, the usual protective system in the form of a further conductivity cell is provided downstream of said sensor, it cannot for example be detected when a concentrate of similar conductivity is used which involves a risk to the patient. A typical possibility of confusion is that between HD concentrate and bleaching solution or disinfectants based thereon and having substantially the same initial conductivity. For this reason conductivity-controlled devices have a second sensor which is based on a different measuring principle, for example a pH sensor as additional protective system. The latter however is not reliable because in operation it can neither be calibrated nor tested. Attention is drawn to corresponding accident reports of the FDA.

On the other hand, hemodialysis apparatuses also exist which operate with volumetric mixing systems in which liquid concentrate and water are mixed together in a predetermined ratio. Such systems have safety technical advantages but cannot readily be changed from operation with a liquid concentrate supplied by the manufacturer with a predetermined composition to a liquid concentrate prepared from pulverulent concentrate and water because the latter concentrate as a rule has a different composition to the former concentrate mentioned.

Furthermore, it has been found that in the preparation of bicarbonate concentrate by mixing with water considerable amounts of $CO_2$ escape and this shifts the equilibrium from bicarbonate to carbonate.

Furthermore, in the container used according to EP-A-0 278 100, which is made rigid, a considerable amount of water is wasted when said container is emptied of the originally present pulverulent concentrate.

The invention is therefore based on the problem of making available an apparatus of the type mentioned at the beginning which is safe and reliable with regard to different concentrates of the same initial conductivity.

According to a further objective the degassing of $CO_2$ in the mixing is to be largely reduced when using bicarbonate as starting powder.

Furthermore, according to a third objective the container containing the pulverulent concentrate is to contain as little water as possible at the end of the mixing operation.

The problem underlying the invention is solved in that the measuring cell is arranged in the conduit which leads from the container to the mixing point and in which the liquid concentrate for mixing with water is disposed.

It has surprisingly been found that even when using concentrates with the same initial conductivity but different chemical composition the safety of the total apparatus is still ensured. For due to different conductivity values of the solutions finally prepared the protective system downstream of the mixing point can detect an incorrect composition. For the apparatus according to the invention first comprises a measuring cell serving for the mixing operation in the form of a conductivity cell in the concentrate conduit which determines the actual value of the concentrate solution generated in the container. Said actual value is compared in a control unit with a predetermined desired value which represents the composition of the finished solution. On the basis of this comparison the solution conveying means, usually a concentrate pump, is correspondingly controlled. This is done in dependence upon the delivery rate at which the water is supplied to the mixing point. This value is also entered into the control unit so that here the ratio concentrate amount/water is predefined.

Secondly, there is the conductivity cell used as protective system arranged downstream of the mixing point and monitoring the finished solution there.

The mode of operation of the apparatus according to the invention will be explained with the aid of an example:

A typical finished sodium bicarbonate solution for a dialysis solution has a conductivity of 2.45 mS/cm and a concentration of 0.035 m/l. It is prepared by 21.2 times dilution from a concentrate containing 0.743 m/l bicarbonate. This solution has a conductivity of 37 mS/cm. Alternatively, other initial concentrations (for example 1 molar, 0.5 molar) and thus other dilutions may be employed.

After the mixing ratio of 21.2 has been fixedly set, the control sensor must be adjusted to a conductivity of 37 mS/cm. Now, if the concentrate is mistaken, sodium chloride being used instead of bicarbonate, a sodium chloride concentrate having a conductivity of 37 mS/cm has a concentration of 0.435 m/l. However, after dilution with the predetermined ratio of 21.2:1 a solution is obtained which has a conductivity of only 2.05 mS/cm. Since the protective system is set to a conductivity value of 2.45 mS/cm with the usual error tolerances of ±5%, this clear mistake can be reliably detected and in the entire apparatus put into the safe state by switching off.

Advantageously, the apparatus according to the invention comprises a temperature sensor which is connected to the container containing the liquid concentrate to correct accordingly the temperature-dependent conductivity value.

The conductivity values of the concentrates and the finished dialysis solution on the basis of bicarbonate are stored in standard table works, for example in CRC Handbook of Chemistry and Physics, and can be stored in the control unit. It is possible to determine therefrom by correlation the desired concentrations of the concentrate and the final solution in dependence upon the delivery rate of the water supplied. Usually, the entire conductivity table of a liquid concentrate system is stored in the control unit and serves there as algorithm for defining the delivery rate of the concentrate pump.

Advantageously, the conductivity measuring cell may be integrated into a concentrate induction tube as described for example in DE-A-37 34 880, to which reference is hereby made for the purposes of disclosure. The system for preparing concentrate from powder and water then comprises a substantially cylindrical receiving means for said induction tube. The particular advantage of this embodiment resides in the possibility of the optional use of liquid and pulverulent concentrate. Since the conductivity cell integrated into the intake or induction tube serves only for distinguishing between concentrates, in one practical embodiment it is constructed without temperature sensor. However, to obtain an exact concentration, as explained above, a temperature compensation should be carried out. For this purpose, in a further specific embodiment the temperature of the water provided for preparing the concentrate is regulated and the temperature of the concentrate measured. In such a case a redundant measurement of concentrate parameters is therefore available.

As already explained, the mixing system of such an apparatus, which apart from the preparation of dialysis solutions can also be used for preparing infusion solutions, comprises a control device which receives a temperature signal of the concentrate/temperature sensor and/or a conductivity signal of the conductivity sensor of the intake tube, a desired concentration signal and a flow desired signal from an adjusting means. On the basis thereof, with the aid of the predetermined algorithm the control means regulates the desired delivery rate of the concentrate pump.

According to a further idea of the invention it has surprisingly been found that the use of degassed water, i.e. water freed from the air dissolved therein, substantially improves the quality of the liquid bicarbonate concentrate. For if air-saturated water is used to prepare liquid bicarbonate concentrates, a great amount of $CO_2$ is liberated and this results in a considerable shift of the bicarbonate/carbonate equilibrium. For this reason, hitherto a considerable amount of acid had to be added to shift the pH value into the acidic region. By using degassed water, the otherwise usual addition of acid from an acid concentrate, admixed as second concentrate and intended to shift the equilibrium in the bicarbonate direction, can be greatly reduced.

Units for degassing dialysis solution are usual in hemodialysis apparatuses. Consequently, these degassing units may be employed; however, the liquid bicarbonate concentrate is not supplied upstream of the degassing unit but on the contrary downstream of said unit. A device for degassing water consists usually of an excess pressure section with which the air dissolved in water is expelled. Advantageously, the water is conducted in recirculation operation, fresh water supplied to a reservoir being recycled to the reservoir through the degassing section and a level control taking place in said reservoir.

According to a further overriding idea of the invention the container containing the powder is made in the form of a collapsible bag which during the use expands and contracts due to the introduction and expulsion of water or solution and at the end of the treatment has only a small filling weight and thus has a low refuse volume.

This bag advantageously comprises an upper inlet tube piece and a lower drain tube piece, to each of which a connector piece is attached which can be connected to a complementary connector piece disposed on the apparatus.

According to a first embodiment the bag is arranged in such a manner that the solution made by mixing with water flows under the action of gravity into a concentrate preliminary container to which the concentrate pump is connected.

In a further embodiment the container containing the powder is supplied with water discontinuously, water first being supplied through an opened inlet valve for a predetermined period of time. The container is thus filled with a predetermined volume of water. Thereafter, said supplied water is allowed to act on the pulverulent salt until a saturated solution is obtained. After this predetermined residence time a discharge valve is actuated so that the saturated solution can flow into a concentrate preliminary container. This operation can take place either during a predetermined open period of the discharge valve or it can be controlled with the aid of a level sensor means disposed on the preliminary container and oscillating between an upper and a lower level value. The latter embodiment is preferred. For this reason the discharge valve is not opened again until the level in the preliminary container has dropped below a lower limit value. Thereupon, filling of the preliminary container starts again. Since the volume between said two level values in the preliminary container is known and the volume of fresh water supplied is predetermined or can be determined by a volume/weight measuring device, at the correct time the inlet valve can be actuated for filling the bag.

As already observed, according to a preferred embodiment the inlet valve is connected to a volume/- weight measuring device so that the amount of water supplied can be determined thereby.

If for example a displacement pickup is used which determines the inflation of the bag on supplying water, the deflection of said displacement pickup is a measure of the amount of liquid supplied. Thus, if the amount of solution contained in the bag drops when the discharge valve is opened the distance covered by the displacement pickup changes, assuming a lower deflection value with increasing dissolving of the salt. In this manner the final dissolving of the salt can be determined, for example in that the initial values of the displacement pickup (in each case unfilled with powder and filled with water for the first time) serve as reference values. If for example at the end of the mixing operation the first difference value is present this indicates a complete dissolving of the originally present salt.

According to a further embodiment the displacement after supplying the water is reduced by a predetermined amount which is correlated with the volume of the salt dissolved. It is presumed here that the density of the salt concentrate remains substantially the same. On the other hand, however, a correction factor in this respect can also be taken into account. Now, if the time dependence of this decrease is recorded in the computer it is readily possible to calculate the final consumption of the salt from said decrease. Thus, at a predetermined time said computer can break off the entire mixing operation just before consumption of the salt and empty the entire bag except for the residual salt constituents.

According to a further embodiment the measuring sensor is employed to monitor the composition. If a pronounced drop of the composition occurs, for example 30% and more, the entire arrangement is switched to the safe state. When this is done the entire bag is pumped by the concentrate pump into a bypass conduit.

On the other hand, solutions of defined compositions may also be prepared from the pulverulent compounds. For this purpose the water inlet valve is opened until a predetermined amount of water sufficing for complete dissolving of the powder contained in the bag has been introduced. As mentioned above, this amount of water can be controlled or regulated with the aid of a volume/amount measuring device. This is then left until a complete dissolving has occurred. Advantageously, the bag provided with powder and water can be activated by mechanical movement (vibrating or squeezing of the bag) or by recirculation of the solution and increasing the water temperature.

The apparatus according to the invention may be used not only for preparing hemodialysis concentrate or hemodialysis solution. On the contrary, it may also be employed for preparing a substitution solution for hemofiltration or an infusion solution.

Also, several of said apparatuses may be combined in order to obtain a multimixing system with which solutions containing several components may be prepared. Such a procedure is appropriate in particular when solutions are to be made from several salts which have a different solubility in water. For this purpose, one apparatus is used for each salt for the stepwise dissolving thereof, the sum of the apparatuses then giving the aforementioned multimixing system.

Advantages, embodiments and features will be apparent from the following description of examples of embodiment.

In the drawings

Figure 2:
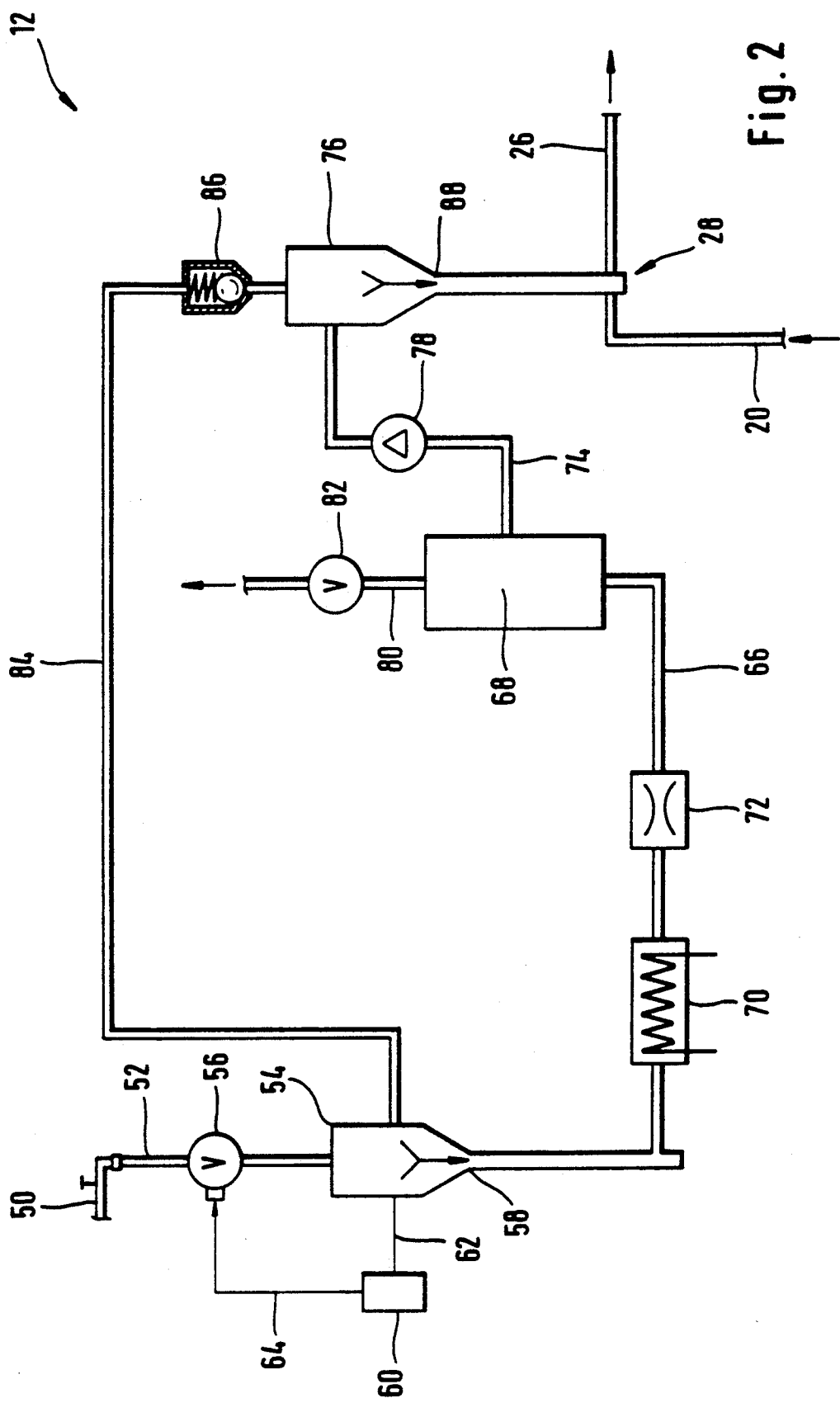
Figure 4:
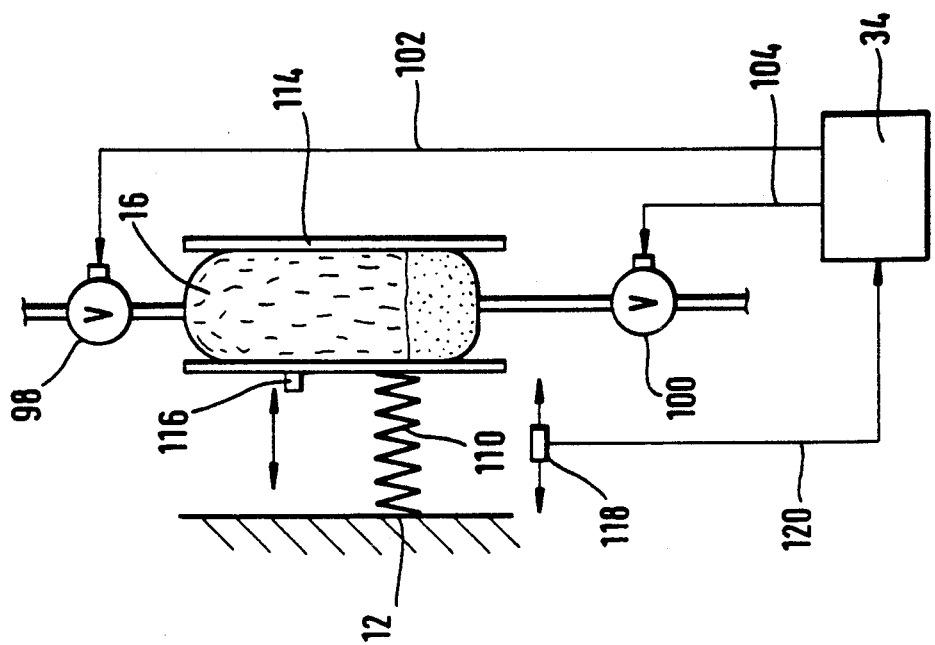
Figure 3:
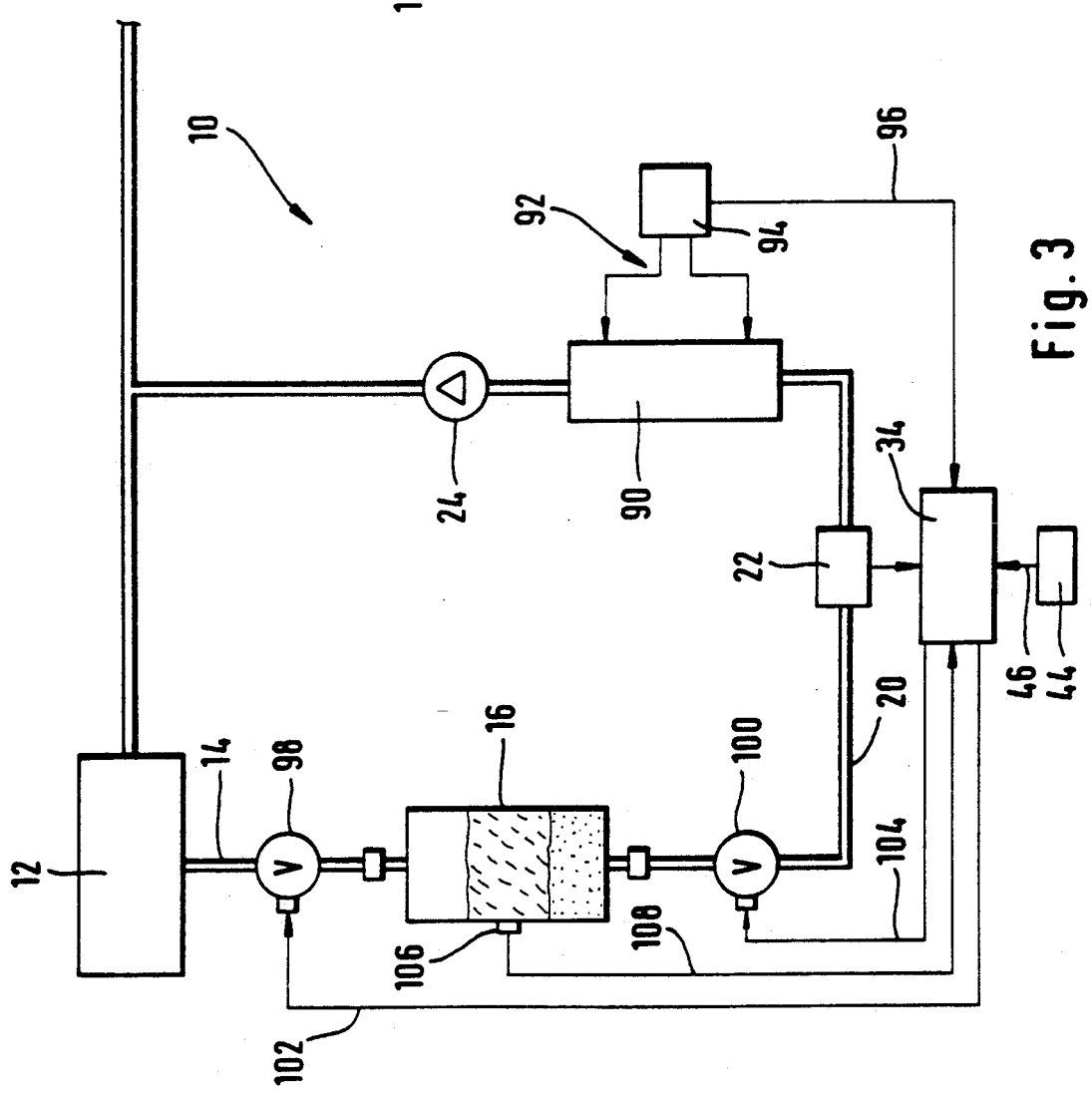

FIG. 1 shows a schematic sketch of the apparatus according to the invention,

FIG. 2 shows a schematic fragment of FIG. 1 representing the water source with the degassing region, FIG. 3 is a schematic view of another embodiment of the invention in which a first filling/discharging operation is illustrated and FIG. 4 shows a schematic cutout of a third embodiment of the invention which relates to a displacement pickup for determining the filling level of the bag according to the invention.

In FIG. 1 an apparatus 10 for preparing medicinal solutions from water and a salt concentrate is schematically illustrated. The apparatus 10 comprises a water source 12 from which a first conduit 14 extends which is connected to a container 16 which contains a salt concentrate 18 in powder form.

The container 16 is advantageously made in the form of a bag.

A second conduit 20 leads from the container 16 and into said conduit a first measuring cell 22 is connected which is advantageously made as conductivity sensor.

Downstream of the first measuring cell 22 a concentrate pump 24 is connected into the second conduit 20 and serves as solution conveying means. Said concentrate pump 24 may also be arranged upstream of the first measuring cell.

Also leading from the water source 12 is a third conduit 26 into which the second conduit 20 opens at the mixing point 28. Downstream of the mixing point 28 a second measuring cell 30 advantageously in the form of a conductivity sensor is connected for monitoring purposes. This is followed by a delivery or balancing means 32 at the end of the third conduit 26 with which the finished liquid mixture is delivered or balanced. For this purpose either a second pump can be used or a balance chamber arrangement as is used for example in the dialyzer of Applicants with the designation A 2008.

Furthermore, a control and regulating means 34 is provided which is connected via lines 36–42 to the first measuring cell 22, the concentrate pump 24, the second measuring cell 30 and the delivery and balancing means 32. Finally, an input unit 44 is provided which is connected via the line 46 to the control and regulating means 34.

For reasons of unity, the control and regulating means is not connected to the means described in FIGS. 3 and 4 for regulating the supply and discharge of the bag 16.

The apparatus 10 shown in FIG. 1 is operated as follows.

From the water source 12, via the conduit 14 fresh water is supplied in which mixing and dissolving of the salt 18 contained therein takes place. The concentrate solution obtained is supplied by the action of the concentrate pump 24 through the conduit 20 to the mixing point 28.

Furthermore, via the third conduit 26 water is supplied to the mixing point 28 and the mixing of the two components takes place there to give the final solution with a predetermined composition. The water is delivered by the conveying means 32, the signals of which are advantageously sent to the control unit 34 via the signal line 42, unless said unit is fixed in its delivery rate. The latter value can however also be fixedly entered into the control unit 34 via the input unit 44.

The unit 34 is also connected to the first measuring cell 22 which determines the actual composition of the liquid concentrate and sends the result to the unit 34. Since said measuring cell 22 is advantageously configured as conductivity sensor, a conductivity value is transmitted which depends only to a first approximation linearly on the concentration (mol. salt/liter water).

For this reason, in the unit 34 a plurality of conductivity data is advantageously stored, said data correlating with the respective concentration values. Since the final solution is defined in its molar concentration, the unit 34 calculates the concentration actual value of the concentrate solution and compares said value with a desired value previously entered via the input unit 44.

The unit 34 is also connected via the line 38 to the concentrate pump 24 which can be varied in its delivery rate by the control unit 34. The concentrate pump 24 is regulated in accordance with the comparison results calculated so that the particular concentrate amount required is supplied to the mixing point 28 with respect to the water amount delivered by the conveying means 32.

Thus, accordingly the concentrate solution delivered by the pump 24 is set to a predetermined conductivity value which is substantially obtained at the first measuring cell 22 itself.

The monitoring takes place through the second measuring cell 30 in the third conduit 26 downstream of the mixing point 28 which in dependence upon the first measuring cell 22 governs the final composition of the solution. If the conductivity value measured differs from the predetermined value by ±5% the entire unit 34 is stopped via the line 40.

As described at the beginning, the apparatus 10 according to FIG. 1 is reliable and safe because the two measuring cells 22 and 30 operate independently of each other and in different concentration ranges. This follows from the fact that concentrates of different composition having the same initial but different final conductivities can be distinguished with certainty.

FIG. 2 shows a specific embodiment of the water source 12. Said water source 12 serves to degas fresh water, as a result of which, as explained at the beginning, a considerably more favourable degassing behaviour of a bicarbonate-containing dialysis solution is obtained.

Firstly, the water source 12 comprises a fresh water connection 50 from which a conduit 52 leads which is connected to a water reservoir 54. A fresh water valve 56 is connected into the conduit 52. The water reservoir 54 has a level regulating means 58 which via the control unit 60 and the two lines 62, 64 cooperates with the fresh water valve 56.

A conduit 66 leads from the fresh water reservoir 54 and opens into the bottom of a degassing container 68. In the conduit 66 a heating means 70 is arranged with which the fresh water is brought to a predetermined temperature, as well as a throttle valve 72.

A further conduit 74 leads from the degassing container 68 and opens into a second water reservoir 76; into said conduit a circulating pump 78 is connected which together with the throttle valve 72 represents a partial vacuum unit acting as degassing unit. Leading from the upper end of the degassing container 68 is a degassing conduit 80 into which a degassing valve 82 is connected which is connected to a partial vacuum unit, not illustrated, for removing the collected expelled air at regular intervals.

The water reservoir 76 comprises at its upper end a recirculation conduit 84 which is led back to the first water reservoir 65 and into which a check valve 86 is connected.

Furthermore, in the second water reservoir 76, which advantageously tapers downwardly, a float arrangement 88 is provided with which a certain medium separation can be effected for the water entering above, as shown in FIG. 2, and the liquid concentrate entering via the concentrate conduit at the lower end. This is advantageous in particular in batch-wise preparation of dialysis solution as is the case in the balance chamber arrangement used by Applicants in the dialysis apparatus A 2008. Consequently, the lower part of the second water reservoir 76 represents the mixing point 28 according to FIG. 1. From this lower part, the third conduit 26 leads away from the mixing point 28 to the consumer, which can represent the delivery or balancing unit 32 illustrated in FIG. 1.

The water source according to FIG. 2 operates as follows:

Firstly, the fresh water valve 56 is opened and the first reservoir 54 filled until the level control means 58 closes the valve 56 via the control unit 60. With the aid of the pump 78 the fresh water is pumped out of the reservoir through the conduit 66, the heating means 70 and the throttle valve 72 into the degassing container 68. Between the throttle 72 and the inlet of the vacuum pump 78 a reduced pressure is generated such that the air physically dissolved in the fresh water is expelled. This air collects in the degassing container 68 and as mentioned above can be removed via the degassing unit 80.

The action of the pump 78 causes the degassed water to pass into the second water reservoir 76 and leave the latter after filling of the reservoir through the recirculation conduit 84 to the first reservoir 54. In the second water reservoir 76 a mixing with the liquid concentrate solution supplied from below takes place, the mixture obtained being discharged through the conduit 26. As already mentioned above this mixing may be continuous if solution is prepared in continuous operation, or alternatively batch-wise, if a balance chamber arrangement is employed as is described for example in DE-OS 2,838,414.

In FIG. 3 a schematic view of a further embodiment of the apparatus 10 according to the invention can be seen with which a first filling and discharge operation can be carried out.

Said apparatus 10 comprises addition ally to the embodiment shown in FIG. 1 between the first measuring cell 22 and the pump 24 a preliminary container 90 on which a level sensor unit 92 is arranged as indicated by the two arrows representing the lower and upper level values. Said level sensor unit 92 is connected via a control unit 94 and a line 96 to the control and regulating unit 34. Furthermore, an inlet valve 98 is connected into the conduit 14 and an outlet valve 100 into the conduit 20, said valves being connected via control lines 102 and 104 to the control unit 34. Finally, a temperature sensor 106 is provided on the container 16 and is connected via a line 108 to the control unit 34.

The unit 10 shown in FIG. 3 is operated as follows:

The inlet valve 98 and the outlet valve 100 are actuated alternately, the outlet valve 100 being deactivated when the upper limit valve of the level sensor 92 is obtained. Similarly, the outlet valve 100 is opened when the level has dropped to the lower value of the level sensor 92.

Since the inner volume of the preliminary container 90 is usually known, and the amount of water admitted by the inlet valve 98 can also be estimated, the control unit 34 is able to open and close the inlet valve 98 in dependence upon the cycles of the outlet valve 100.

Attention is otherwise drawn to the further modes of operation as already explained above.

Finally, it may be expedient for the measuring cell 22 arranged in the apparatus according to FIG. 3 upstream of the preliminary container 90 to be arranged alternatively downstream of said preliminary container or also following the concentrate pump 24.

FIG. 4 illustrates another embodiment with which the degree of filling of the container 16 constructed as bag can be determined. The same reference numerals as in FIGS. 1 to 3 are again used.

To determine the degree of filling a displacement pickup means 110 is employed which consists of the frame members 112 and 114 as rigid base members of a pressure means 116 consisting of a pressure plate which presses against the container 16 constructed as bag, and a pressure spring secured against the frame member 112, as well as a measuring cell 118 for determining the distance covered. Said measuring cell 118 is connected via the line 120 to the control unit 34 and transmits the displacement signal picked up thereto.

The embodiment according to FIG. 4 is operated as follows:

The pressure means 110 first compresses the bag 16 so that as a result the distance between the pressure plate 116 and the frame member 114 can be considered as a parameter for the quantities disposed in the bag 16. Consequently, said signal can be processed by the control unit 34. In particular the empty state of the bag 16 may first be determined, which is filled then only with the pulverulent substance. Likewise, after the first filling operation with water the deflection of the pressure plate 116 can be determined as remains as absolute value at the end of the mixing operation, i.e. the distance apart of the two members 114 and 116 corresponds substantially to this signal and the control unit 34 can thereby terminate the mixing operation.

On the other hand, however, it is also possible as explained above to determine the stepwise decrease of the distance between said two members 114 and 116.

Instead of the displacement pickup 110 a weighing arrangement may also be employed on which the bag 16 is suspended. In this case as well, the initial weight with and without supplying a certain amount of water can be determined and stored in the control unit 34. Attention is otherwise drawn to the above explanations.

I claim:

1. Apparatus for preparing a medicinal solution, in particular dialysis solution, from a pulverulent concentrate and water, comprising a water source, a first conduit from the water source to a container containing the pulverulent concentrate, a second conduit extending from the container to a mixing point which is located in a third conduit originating from the water source, a means for controlling the flow of the concentrate solution connected into the second conduit, a solution conveying means in the third conduit downstream of the mixing point, a first measuring cell in the conduit system, a control unit controlling the means for controlling the flow of the concentrate solution in predetermined manner in response to the signal of the first measuring cell such that the dialysis solution generated at the mixing point corresponds to a predetermined composition, and a protective system which comprises a second measuring cell and which is arranged downstream of the mixing point and switches off the apparatus in the event of an incorrect composition of the dialysis solution, characterized in that the first measuring cell (22) is connected into the second conduit (20).

2. Apparatus according to claim 1, characterized in that the first and second measuring cells (22, 30) are each a conductivity cell.

3. Apparatus according to claim 1 or 2, characterized in that a control and regulating unit (34) is connected to the first measuring cell (22) and compares the signal thereof as actual value with a desired value and on the basis of the result of the comparison controls a concentrate pump (24) as means for regulating the flow of concentrate solution.

4. Apparatus according to claim 1, characterized in that in the second conduit (20) upstream of a concentrate pump (24) for regulating flow of concentrate solution a preliminary container (90) is arranged to which a level sensor unit (92) is attached, that upstream of the container (16) an inlet valve (98) is connected into the first conduit (14) and downstream of the container (16) an outlet valve (100) is connected into the second conduit (20) and that in response to the signal of the level sensor unit (92) the control unit (34) activates or deactivates the inlet valve (98) and the outlet valve (100) in predetermined manner.

5. Apparatus according to claim 1 or 4, characterized in that the container (16) is constructed as bag.

6. Apparatus according to claim 1, characterized in that the container (16) is attached to a measuring device for continuous determination of amount of water added to the container, said device transmitting a signal to the means for controlling the flow of the concentrate solution.

7. Apparatus according to claim 6, characterized in that the container is constructed as a bag and is arranged in a displacement pickup means (110).

8. Apparatus according to claim 5, characterized in that the container (16) is attached to a measuring device for continuous determination of amount of water added to the container, said device transmitting a signal to the means for controlling the flow of the concentrate solution.

* * * * *